United States Patent [19]

Kosley, Jr. et al.

[11] Patent Number: 5,177,207

[45] Date of Patent: Jan. 5, 1993

[54] 7-ARYL AND HETEROARYL ETHERS OF DESACETYLFORSKOLIN

[75] Inventors: Raymond W. Kosley, Jr., Bridgewater, N.J.; Gerard O'Malley, Newtown, Pa.; Bettina Spahl, Edison, N.J.

[73] Assignee: Hoechst-Roussel Pharmaceuticals, Inc., Somerville, N.J.

[21] Appl. No.: 616,872

[22] Filed: Nov. 21, 1990

Related U.S. Application Data

[62] Division of Ser. No. 295,840, Jan. 11, 1989, Pat. No. 4,999,351.

[51] Int. Cl.$^5$ .............. C07D 319/08; C07D 473/26; C07D 217/22
[52] U.S. Cl. .............................. 544/276; 544/298; 544/316; 544/319; 549/358; 546/141; 546/153; 546/157; 546/158; 546/270; 548/187; 548/213; 548/225; 548/228; 548/229; 548/243
[58] Field of Search ............... 549/358; 514/452, 453, 514/262, 267, 274, 312, 309, 338, 369, 372, 380, 376; 548/225, 228, 229, 243, 187, 213; 544/276, 298, 316, 319; 546/141, 153, 157, 158

[56] References Cited

U.S. PATENT DOCUMENTS

| | | | |
|---|---|---|---|
| 4,088,659 | 5/1978 | Bhat et al. | 260/345.2 |
| 4,118,508 | 10/1978 | Bhat et al. | 424/283 |
| 4,134,986 | 1/1979 | Bajwa et al. | 424/283 |
| 4,476,140 | 10/1984 | Sears et al. | 424/283 |
| 4,517,200 | 5/1985 | Kreutner et al. | 514/455 |
| 4,564,626 | 1/1986 | Kreutner et al. | 514/430 |
| 4,639,443 | 1/1987 | Kosley, Jr. et al. | 514/222 |
| 4,639,446 | 1/1987 | Kosley, Jr. et al. | 514/222 |
| 4,666,904 | 5/1987 | Kosley, Jr. et al. | 514/222 |
| 4,672,115 | 6/1987 | Kosley, Jr. et al. | 544/58.2 |
| 4,673,752 | 6/1987 | Kosley, Jr. et al. | 549/389 |
| 4,677,103 | 6/1987 | Kosley, Jr. et al. | 514/222 |
| 4,999,351 | 3/1991 | Kosley, Jr. et al. | 514/228.2 |

FOREIGN PATENT DOCUMENTS

| | | |
|---|---|---|
| 0126313A2 | 11/1984 | European Pat. Off. |
| 223308 | 8/1985 | European Pat. Off. |
| 0189801A1 | 8/1986 | European Pat. Off. |
| 0192056A1 | 8/1986 | European Pat. Off. |
| 0257631 | 3/1988 | European Pat. Off. |
| 0294695 | 12/1988 | European Pat. Off. |
| 0297496 | 1/1989 | European Pat. Off. |
| 0315097 | 5/1989 | European Pat. Off. |
| 3346869A1 | 7/1984 | Fed. Rep. of Germany |
| 3407514A1 | 9/1985 | Fed. Rep. of Germany |
| 3502686A1 | 8/1986 | Fed. Rep. of Germany |

OTHER PUBLICATIONS

Chemical Abstracts, vol. 111, No. 15, Oct. 9, 1989, Columbus, Ohio, USA Nippon Kayaku Co., Ltd.: "Forskol in Derivatives as Antihypertensives and Adenylate Cyclas Activators", p. 800, col. 1, Abstract No. 134 576j & Jpn. Kokai Tokkyo Koho JP 01 09 986 (89 09 986).

W. Colucci et al., New Positive Inotropic Agents in the Treatment of Congestive Heart Failure, *New England Journal of Medicine*, 314(6), 349-358 (1986).

Sequin et al., "Effect of Novel 7-β-Derivative . . . ", CA 109: 446u (1988).

J. Caprioli et al., "Forskolin Lowers Intraocular Pressure by Reducing Aqueous Inflow", Invest. Ophtalmol. & Vis. Sci., 25, 268-277 (1984).

N. de Souza et al., "Forskolin: A Labdane Diterpenoid With Antihypertensive, Positive Inotropic, Platelet Aggregation Inhibitory, and Adenylate Cyclase Activating Properties", Med. Res. Rev., 3(2), 201-219 (1983).

S. Bhat et al., "The Antihypertensive and Positive Inotropic Diterpene Forskolin: Effects of Structural Modifications on its Activity", J. Med. Chem., 26 486-492 (1983).

K. Seamon et al., "Structure-Activity Relationships for Activation of Adenylate Cyclase by the Diterpene Forskolin and Its Derivatives", J. Med. Chem., 26(3), 436-439 (1983).

S. Bhat et al., "Reactions of Forskolin, a Biologically Active Diterpenoid From *Coleus forskohlii*", J. Chem. Soc., Perkin I, 767-771 (1982).

K. Seamon and J. Daly "Activation of Adenylate Cyclase by the Diterpene Forskolin Does Not Require the Guanine Nucleotide Regulatory Protein", J. Bio. Chem., 256(19), 9799-9801 (1981).

J. Takeda et al., "Forskolin Activates Adenylate Cyclase Activity and Inhibits Mitosis in In Vitro in Pig Epidermis", J. Investig. Derm., 81(3), 236-240 (1981).

K. Seamon et al., "Forskolin: Unique Diterpene Activator of Adenylate Cyclase in Membranes and in Intact Cells", Proc. Natl. Acad. Sci., 78(6), 3363-3367 (1981).

S. Bhat et al., "Structures and Sterochemistry of New Labane Diterpenoids from *Coleus forskohliii* Briq.", Tet. Lett., No. 19, 1669-1672 (1977).

Derwent Citation 85-223308/36, 231 "Treatment of Hyperplastic Skin Diseases, Especially Psoriasis, by Topical Application of Labdane Derivatives, Especially Forskolin".

*Primary Examiner*—C. Warren Ivy
*Assistant Examiner*—Amelia A. Owens
*Attorney, Agent, or Firm*—Curtis, Morris & Safford

[57] ABSTRACT

Novel forskolin derivatives, intermediates and processes for the preparation thereof, and methods for treating cardiac failure and memory deficit utilizing compounds or compositions thereof are disclosed.

16 Claims, No Drawings

7-ARYL AND HETEROARYL ETHERS OF DESACETYLFORSKOLIN

This application is a division of application Ser. No. 295,840, filed Jan. 11, 1989 now U.S. Pat. No. 4,999,351.

The present invention relates to forskolin derivatives. More particularly, the present invention relates to 7-aryl and heteroaryl ethers of desacetylforskolin and derivatives of formula I

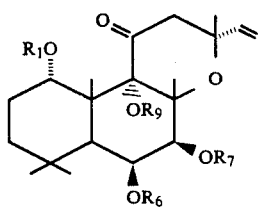

wherein
- $R_1$ is hydrogen, loweralkyl, arylloweralkyl, a group of formula $R_3R_4R_5Si$, a group of formula $R_8CO$, or a group of formula $R_{10}R_{11}N(CHR_{12})_nCO$ wherein n is 0 or 1;
- $R_6$ is hydrogen, a group of formula $R_{13}CO$ or a group of formula $R_{14}R_{15}NCO$;
- $R_7$ is phenyl, naphthyl, furanyl, oxazolyl, thiazolyl, pyridinyl, pyrimidinyl, purinyl, quinolinyl, or isoquinolinyl, each of which is unsubstituted or mono- or poly-substituted by loweralkyl, halogen or nitro;
- $R_9$ is hydrogen; or
- $R_1$ and $R_9$ taken together form a group of formula CO, a group of formula SO or a group of formula $CHNR_{17}R_{18}$;
- $R_3$, $R_4$ and $R_5$ are the same or not all the same and each is hydrogen or loweralkyl;
- $R_8$ is hydrogen or loweralkyl;
- $R_{10}$, $R_{11}$ and $R_{12}$ are the same or not all the same and each is hydrogen, loweralkyl or arylloweralkyl; or
- $R_{10}$ and $R_{11}$ taken together with the nitrogen atom to which they are attached form a group of formula

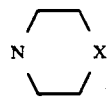

wherein
X is CO, O, S, a group of the formula $CHR_{19}$ or a group of formula $NR_{20}$;
- $R_{13}$ is hydrogen or loweralkyl;
- $R_{14}$ is hydrogen, loweralkyl, hydroxyloweralkyl, loweralkoxyloweralkyl, or a group of formula $HOCH_2CH(OH)CH_2$;
- $R_{15}$ is hydrogen, loweralkyl, hydroxyloweralkyl, loweralkoxyloweralkyl, a group of formula

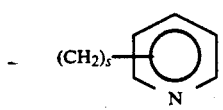

wherein s is 1 or 2, a group of formula

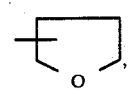

a group of formula $HOCH_2CH(OH)CH_2$, or a group of formula $(CH_2)_tNR_{21}R_{22}$ wherein t is an integer from 2 to 6;
- $R_{17}$ and $R_{18}$ are the same or different and each is loweralkyl; or
- $R_{17}$ and $R_{18}$ taken together with the nitrogen atom to which they are attached form a group of formula

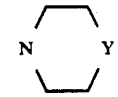

wherein Y is O or S;
- $R_{19}$ is hydrogen, loweralkyl or $OR_{23}$;
- $R_{20}$ is loweralkyl;
- $R_{21}$ and $R_{22}$ are the same or different and each is loweralkyl; or
- $R_{21}$ and $R_{22}$ taken together with the nitrogen atom to which they are attached form a group of formula

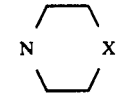

wherein X is as above;
- $R_{23}$ is hydrogen or $COR_{24}$;
- $R_{24}$ is loweralkyl; and the optical and geometric isomers thereof, or a pharmaceutically acceptable salt thereof.

The present invention also relates to compounds of formula II

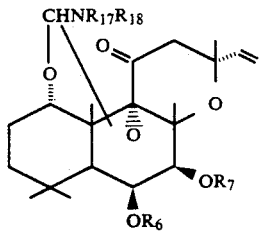

wherein $R_6$, $R_7$, $R_{17}$ and $R_{18}$ are as hereinbeforedefined, which are useful as intermediates in the preparation of the forskolin derivatives of the present invention. Preferably, $R_{17}$ and $R_{18}$ are methyl.

Subgeneric to the forskolin derivatives of the present invention are compounds of formula I wherein:
(a) $R_1$ and $R_9$ taken together form a group of the formula $CHNR_{17}R_{18}$ where $R_{17}$ and $R_{18}$ are the same or different and each is loweralkyl, preferably methyl;
(b) $R_1$ is hydrogen;
(c) $R_6$ is hydrogen;
(d) $R_1$, $R_6$ and $R_9$ are hydrogen;
(e) $R_6$ is $CONR_{16}(CH_2)_uNR_{25}R_{26}$ wherein $R_{16}$ is hydrogen or loweralkyl, preferably hydrogen, and $R_{25}$ and $R_{26}$ are the same or different and each is hydrogen or loweralkyl, preferably methyl, and u is an integer from 2 to 5, preferably 2 or 3;

(f) $R_1$ and $R_9$ are hydrogen and $R_6$ is $CONR_{16}(CH_2)_uNR_{25}R_{26}$ wherein $R_{16}$ is hydrogen or loweralkyl, preferably hydrogen, and $R_{25}$ and $R_{26}$ are the same or different and each is hydrogen or lower alkyl, preferably methyl, and u is an integer from 2 to 5, preferably 2 or 3;

(g) $R_7$ is phenyl which is mono- or poly-substituted by nitro, an example being para-nitrophenyl;

(h) $R_7$ is pyridinyl, an example being 2-pyridinyl, or pyridinyl which is mono- or poly-substituted by halogen, an example being 2-(6-fluoropyridin-2-yl);

(i) $R_7$ is pyrimidinyl, an example being pyrimidin-2-yl, or pyrimidinyl which is mono- or poly-substituted by halogen, an example being 2-chloropyrimidin-4-yl; and (j) $R_7$ is purinyl or purinyl which is mono- or poly-substituted by loweralkyl, preferably methyl, an example being 1-methylpurin-6-yl.

As used throughout the specification and appended claims, the term "alkyl" refers to a straight or branched chain hydrocarbon radical containing no unsaturation and having 1 to 8 carbon atoms such as methyl, ethyl, 1-propyl, 2-propyl, 2-methylpropyl, 1-pentyl, 2-pentyl, 3-hexyl, 4-heptyl, 2-octyl, and the like. The term "alkenyl" refers to a straight or branched chain hydrocarbon radical containing one or more double bonds and having 1 to 8 carbon atoms such as propenyl, pentenyl, hexenyl, and the like. The term "alkanol" refers to a compound formed by a combination of an alkyl group and a hydroxy radical and includes, for example, methanol, ethanol, 1- and 2-propanol, 1, 2-dimethylethanol, hexanol, octanol, and the like. The term "alkoxy" refers to a compound formed by a combination of an alkyl group and a hydroxy group and includes, for example, methoxy, ethoxy, propoxy, butoxy, and the like. The term "alkoxide" refers to a compound formed by the combination of an alkoxy group and a metal and includes, for example, potassium t-butoxide. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid and the like. The term "halogen" refers to a member of the family consisting of fluorine, chlorine, bromine or iodine. The term "lower" as applied to any of the aforementioned groups refers to a group having a carbon skeleton containing up to and including six carbon atoms. The term "aryl" refers to an organic radical derived from an aromatic hydrocarbon by the removal of one hydrogen atom, such as, e.g., phenyl, tolyl, salicyl, napthyl, etc.

In the formulas presented herein, the various substituents are illustrated as joined to the forskolin nucleus by one of two notations: a solid line (—) indicating a substituent which is in the $\beta$-orientation (i.e., above the plane of the molecule) and a broken line (---) indicating a substituent which is in the $\alpha$-orientation (i.e., below the plane of the molecule). The formulas have all been drawn to show the compounds in their absolute stereochemical configuration. Inasmuch as the starting materials having a forskolin nucleus are naturally occurring or are derived from naturally occurring materials, they, as well as the final products, have a forskolin nucleus existing in the single absolute configuration depicted herein. The processess of the present invention, however, are intended to apply as well to the synthesis of forskolin derivatives of the racemic series.

In addition to the optical centers of the forskolin nucleus, the substituents thereon may also contain chiral centers contributing to the optical properties of the compounds of the present invention and providing a means for the resolution thereof by conventional methods, for example, by the use of optically active acids. The present invention comprehends all optical isomers and racemic forms of the compounds of the present invention, where such compounds have chiral centers in addition to those of the labdane nucleus.

The novel forskolin derivatives of the present invention are synthesized by the representative processes illustrated in Reaction Schemes A and B immediately preceding the claims.

Referring to Scheme A, compounds of formula 3 are prepared by reacting a compound of formula 1 (e.g., 7-desacetylforskolin 1,9-dimethylformamide acetal) with a compound of formula $R_7$-Hal, wherein $R_7$ is as hereinbeforedefined and Hal is halogen, to provide arylether 2 which is then hydrolyzed by treatment with a mixture of an alkanol and water or a mixture of an alkanol, water and acetic acid to afford compound 3.

The arylation of compound 1 is readily accomplished by treating compound 1 with an aryl- or heteroaryl halide in the presence of a metal alkoxide. Aryl- or heteroaryl halides used in accordance with the invention have the formula $R_7$-Hal, wherein $R_7$ is as hereinbeforedefined and Hal is halogen, and include, for example, 2-fluoropyridine, 2-chloropyrimidine, 2,6-difluoropyridine, 1-fluoro-4-nitrobenzene, 2,4-dinitrofluorobenzene, 2,4-dichloropyrimidine and 6-chloro-1-methyl-purine. The arylation is conducted in a number of solvents well known in the art. Of these solvents, tetrahydrofuran is preferred. Metal alkoxides used in accordance with the invention include a number of substances well known in the art, potassium t-butoxide being preferred. While the temperature at which the arylation is performed is not narrowly critical, it is preferred to conduct the reaction at a temperature ranging from about $-20°$ to $100°$ C. It is most preferred to perform the arylation at a temperature ranging from about $0°$ to $50°$ C.

The deacetalation is effected by hydrolyzing compound 2 with a mixture of an alkanol and water or a mixture of an alkanol, water and acetic acid. Among the alkanols, there may be mentioned, for example, methanol, ethanol and propanol. Methanol is the preferred alkanol. While the proportion of alkanol to water is not narrowly critical, a proportion of 3:1 is preferred. Deacetalation proceeds at a temperature ranging from about $0°$ to $100°$ C. with a temperature ranging from about $60°-70°$ C. being preferred.

Referring to Scheme B, compounds of formula 6 are prepared in the same manner as compounds of formula 3 except that instead of using a compound of formula 1, a compound of formula 4 is used wherein $R_6$ is as hereinbeforedefined.

The starting materials for the processes of the present invention as shown in Scheme A, i.e., forskolin derivatives of formula 1, are described in U.S. Pat. No. 4,639,443, issued Jan. 27, 1987, the disclosure of which is incorporated herein by reference. The starting materials for the processes of the present invention as shown in Scheme B, i.e., forskolin derivatives of formula 4, are described in U.S. Ser. No. 137,998, filed Dec. 28, 1987, the disclosure of which is incorporated herein by reference.

U.S. Pat. Nos. 4,639,446, issued Jan. 27, 1987, 4,666,904, issued May 19, 1987, 4,672,115, issued Jun. 9, 1987, 4,673,752, issued Jun. 16, 1987, and 4,677,103, issued Jun. 30, 1987, the disclosure of each of which patents is incorporated herein by reference, disclose a variety of methods which can be used for further derivatization of forskolin compounds 3 and 6 of the present invention at the 1-position. The disclosure of U.S. Ser. No. 137,998 also discloses methods which can be used for further derivatization of compounds 3 and 6 of the present invention at the 1-position. In particular, these methods can be used to prepare compounds of the invention wherein $R_1$ is $R_3R_4R_5Si$, $R_8CO$ and $R_{10}P_{11}N(CHR_{12})_nCO$ wherein $R_3$, $R_4$, $R_5$, $R_8$, $R_{10}$, $R_{11}$ and n are hereinbeforedefined. S. V. Bhat et al., "The Antihypertensive and Positive Inotropic Diterpene Forskolin: Effects of Structural Modifications on Its Activity", J. Med. Chem., 26, 487–493 (1983) and S. V. Bhat et al., "Reactions of Forskolin, A Biologically Active Diterpenoid from *Coleus forskolii*", J. Chem. Soc., Perkin I, 767–771 (1982) disclose methods for derivatization of compounds 3 and 6 of the present invention at the 1-position wherein $R_1$ is loweralkyl or arylloweralkyl.

The aryl and heteroaryl ethers of desacetylforskolin of the present invention are useful in the treatment of cardiac failure by virtue of their ability to elicit a positive inotropic effect as evidenced by an increase in contractile force in an isolated guinea pig atria assay which is performed as follows:

Male guinea pigs weighing 200–300 grams are stunned with a blow to the back of the head. The heart is rapidly removed and placed in a petri dish containing Kreb's solution. The ventricle is separated from the atria, the atria are sectioned in the right and left atria, and double-O silk ligatures are tied to the apex of the left atrium. The atrium is fixed to a pair of platinum plate electrodes and suspended in a 20 ml tissue bath containing Kreb's solution aerated with 95% oxygen-5% carbon dioxide at 37° C. One end of the atrium is fixed to a hook in the electrode and the other end is connected to a Grass FTO3 force displacement transducer. Resting tension and stabilization time are the same as described above. The atrium is stimulated at 3 Hz, 0.5 msec duration at supramaximal voltage (constant current) via a Grass S88 stimulator and constant current unit. Force of contraction is continuously displaced on a Gould recorder. Test drug is prepared as in section A and is added to the tissue baths in the same fashion. Change in contractile force from baseline is determined for each concentration, and the change in contractile force (g) is plotted against accumulated drug concentration (µg/ml). The activity of the test drug, i.e., the increase in contractile force (g) from the stabilized force expressed as the percentage change at a given concentration is determined graphically, as is the $ED_{50}$-value, i.e., the extrapolated dose (µg/ml) which increases the contractile force by 50% over the stabilized rate.

Results obtained in this assay for representative compounds of the invention and a reference compound are presented in the Table.

TABLE

| COMPOUND | CONCENTRATION (µg/ml) | INOTROPIC ACTIVITY (% Change of Contractile Force) |
|---|---|---|
| A[1] | 0.009[2] | 50 |
| B[3] | 0.01[2] | 50 |
| C[4,5] | 0.073[2] | 50 |

[1] 7-Desacetyl-6-(2-dimethylaminoethylaminocarbonyl)-7-(pyridin-2-yl) forskolin hydrochloride hydrate
[2] Extrapolated $ED_{50}$ value
[3] 7-Desacetyl-7-(pyrimidin-2-yl) forskolin
[4] Forskolin
[5] Reference Compound Cardiac failure treatment is achieved when the forskolin derivatives of the present invention are administered to a subject requiring such treatment as an effective oral, parenteral or intravenous dose of from about 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosage set forth herein are exemplary only and that they do not, to any extent, limit the scope of practice of the invention.

Compounds of the present invention are also useful for the treatment of memory loss, hypertension, bronchial asthma, glaucoma and psoriasis.

Compounds of the present invention include:

7-desacetyl-6-(3-dimethylaminopropylaminocarbonyl) (pyrimidin-yl)forskolin;

7-desacetyl-6-(4-dimethylaminobutylaminocarbonyl) (pyrimidin-2-yl)forskolin;

7-desacetyl-7-[2-(3-dimethylaminopropylamino)pyrimidin-4-yl]forskolin 7-desacetyl-7-[2-(2-dimethylaminoethylamino)pyrimidin-4-yl]forskolin 6-acetyl-7-desacetyl-7-(pyrimidin-2-yl)forskolin;

7-desacetyl-7-(2-chloropyrimidin-4-yl)forskolin;

7-desacetyl-7-(pyrimidin-2-yl)forskolin-6-methylether;

7-desacetyl-6-(methylaminocarbonyl)-7-(pyrimidin-2-yl)forskolin;

7-desacetyl-7-(pyrimidin-4-yl)forskolin;

7-desacetyl-7-(2-hydroxypyrimidin-4-yl)forskolin;

7-desacetyl-7-(4-aminophenyl)forskolin;

7-desacetyl-6,7-bis(4-aminophenyl)forskolin;

7-desacetyl-7-(4-dimethylaminophenyl)forskolin;

7-desacetyl-6-(3-aminopropylaminocarbonyl)-7-(pyrimidin-2-yl)forskolin;

7-desacetyl-6-(2-aminoethylaminocarbonyl)-7-(pyrimidin-2-yl)forskolin;

7-desacetyl-7-(2-aminophenyl)forskolin; and 7-desacetyl-6-(3-dimethylaminopropylaminocarbonyl)-7-(pyridin-2-yl)forskolin.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to material of the above type, a liquid carrier such as a fatty oil. Other dosage unit forms may contain other various materials which modify the physical form of the dosage unit, such as, for example, coatings. Thus tablets or pills may be coated with sugar, shellac or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 5% of the weight thereof. The amount of active compound in such compositions is such that a suitable dosage will be obtained. Preferred compositions and preparations according to the present invention are prepared so that a parenteral dosage unit contains between 0.001 to 10 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparations can be enclosed in disposable syringes or multiple dose vials made of glass or plastic.

The following examples are for illustrative purposes only and are not to be construed as limiting the invention. All temperatures are given in degrees Centigrade.

EXAMPLE 1

Preparation of 7-Desacetyl-7-(pyridin-2-yl)forskolin 1,9-dimethylformamide acetal To a stirred solution of 1.00 g (2.36 mmol) of 7-desacetylforskolin 1,9-dimethylformamide acetal in 10 ml of dry tetrahydrofuran was added 250 mg (2.23 mmol) of potassium t-butoxide. To the suspension was added an additional 20 ml of tetrahydrofuran followed by 0.20 ml (0.23 g, 2.33 mmol) of 2-fluropyridine and the suspension was then stirred at room temperature under nitrogen for 0.5 hr and at 60°-65° for 2.5 hr. The solution was cooled to room temperature, 25 mg (0.22 mmol) of potassium t-butoxide was added followed by 0.05 ml (0.057 g, 0.57 mmol) of 2-fluororopyridine and the resulting solution was stirred at 60°-65° for 0.5 h and allowed to cool to room temperature. The solution was poured into ice water/ether, extracted twice with ether, washed with water, saturated sodium chloride, dried over sodium sulfate and filtered. Evaporation of the solvent provided an oil which was dissolved in a minimum volume of ethyl acetate and flash chromatographed on silica gel, eluting with 25% ethyl acetate/hexane. The product-containing fractions were combined and concentrated to a white solid which was recrystallized from cyclohexane to provide 0.536 (1.07 mmol, 45.3%) of colorless needles of 7-desacetyl-7-(pyrid-2-yl)forskolin 1,9-dimethylformamide acetal, mp 151°-164°. The material appeared pure by thin layer chromatography on silica gel: 25% ethyl acetate/hexane, $R_f=0.15$; 30% acetone/hexane, $R_f=0.4$. IR(CHCl$_3$), NMR(CDCl$_3$) and mass spectra (MH$^+$=501) were consistent with the assigned structure.

ANALYSIS: Calculated for $C_{28}H_{40}N_2O_6$: 67.17% C, 8.05% H, 5.60% N. Found: 67.61% C, 8.11% H, 5.60% N.

EXAMPLE 2

Preparation of 7-Desacetyl-7-(pyridin-2-yl)forskolin

A suspension of 1.0 g (2.0 mmol) of 7-desacetyl-7-(pyridin-2-yl)forskolin 1,9-dimethylformamide acetal (prepared as described in Example 1) in 50 ml of 3/1 methanol/water was stirred at 60°-70° for 40 hr. The solution was allowed to cool to room temperature and concentrated to an oil. The oil was dissolved in ethyl acetate and flash chromatographed on silica gel, eluting with 25% ethyl acetate/hexanes. The product-containing fractions were combined and concentrated to an oil which was recrystallized from ethyl acetate/hexanes to provide 0.372 g (0.832 mmol, 41.6%) of 7-desacetyl 148°-151°. The material appeared pure by thin layer chromatography on silica gel: 25% ethyl acetate/hexane, $R_f=0.14$; 2% methanol dichloromethane $R_f=0.27$. IR(CHCl$_3$), NMR(CDCl$_3$) and mass spectra (MH$^+$=446) were consistent with the assigned structure.

ANALYSIS: Calculated for $C_{25}H_{35}NO_6$: 67.39% C, 7.92% H, 3.14% N. Found: 67.52% C, 7.90% H, 3.11% N.

EXAMPLE 3

Preparation of
7-Desacetyl-7-(6-fluoropyridin-2-yl)forskolin
1,9-dimethylformamide acetal To a stirred solution of 5.0 g (11.8 mmol) of 7-desacetylforskolin 1,9-dimethyformamide acetal in 100 ml of dry tetrahydrofuran under nitrogen was added 1.33 g (11.9 mmol) of potassium t-butoxide. The suspension was stirred for one min under nitrogen and 1.28 ml (14.1 mmol) of 2,6-difluoropyridine was added. The suspension gradually dissolved over 45 min after which the solution was stirred for an additional 15 min, and then poured into ice/water/ethyl acetate. To the mixture was then added saturated sodium chloride, and the organic layer was separated, dried over sodium sulfate, filtered and concentrated to an oil. The oil was purified by flash chromatography on silica gel, eluting with 30% ethyl acetate/hexanes. The product-containing fractions were combined and concentrated to provide, after recrystallization from cyclohexane/ethyl acetate, 2.19 g (4.22 mmol, 35.8%) of 7-desacetyl-7-6-fluoropyridin-2-yl)forskolin 1,9-dimethylformamide acetal, m.p. 178–181. The material appeared pure by thin layer chromatography on silica gel: 20% ethyl acetate/hexanes, $R_f=0.11$; 1% methanol/dichloromethane, $R_f=0.12$. IR(CHCl$_3$), NMR(CDCl$_3$) and mass spectra (MH+ =519) were consistent with the assigned structure.

ANALYSIS: Calculated for $C_{28}H_{39}FN_2O_6$: 64.85% C, 7.58% H, 5.40% N. Found: 65.07% C, 7.55% H, 5.41% N.

EXAMPLE 4

Preparation of
7-Desacetyl-7-(6-fluoropyridin-2-yl)forskolin

A solution of 1.2 g (2.31 mmol) of 7-desacetyl-7-(6-fluoropyridin-2-yl)forskolin 1,9-dimethylformamide acetal (prepared as described in Example 3) in 60 ml methanol and 20 ml of water was stirred at 60°–70° for 72 hr. The solution was allowed to cool to room temperature and concentrated to an oil. The oil was dissolved in ethyl acetate, dried over sodium sulfate, filtered and again concentrated to an oil. The material was dissolved in a minimum volume of ethyl acetate and flash chromatographed on silica gel, eluting with 20% ethyl acetate/hexanes followed by 30% ethyl acetate/hexanes. The product-containing fractions were combined and concentrated to an oil which was crystallized from cyclohexane/ethyl acetate to provide, in two crops, 0.69 g (1.49 mmol, 64.5%) of 7-desacetyl-7-(6-fluoropyridin-2-yl)forskolin, mp 166°–168°. The material appeared pure by thin layer chromatography on silica gel: 30% ethyl acetate/hexanes, $R_f=0.17$; 2% methanol/dichloromethane, $R_f=0.2$. IR(CHCl$_3$), NMR(CDCl$_3$) and mass spectra (MH+ =464) were consistent with the assigned structure.

ANALYSIS: Calculated for $C_{25}H_{34}FNO_6$: 64.78% C, 7.39% H, 3.02% N. Found: 64.56% C, 7.30% H, 3.05% N.

EXAMPLE 5

Preparation of 7-Desacetyl-7-(pyrimidin-2-yl)forskolin
1,9-dimethylformamide acetal To a stirred solution of 5.0 g (11.8 mmol) of 7-desacetylforskolin 1,9-dimethylformamide acetal in 100 ml of dry tetrahydrofuran was added 1.33 g (11.6 mmol) of potassium t-butoxide. The suspension was stirred at room temperature for several minutes and 1.6 g (14.0 mmol) of 2-chloropyrimidine was added. The mixture was stirred 3 hr at room temperature, poured into ice/water/dichloromethane and the organic layer was separated, washed with sodium chloride and concentrated in vacuo. The residue was dissolved in a minimum volume of ethyl acetate and flash chromatographed on silica gel, eluting with 30% ethyl acetate/hexane. The fractions were combined and concentrated in vacuo, leaving a solid which was recrystallized from cyclohexane/ethyl acetate to provide 2.00 g (3.99 mmol, 33.8%) of 7-desacetyl-7-(pyrimidin-2-yl)forskolin, mp 200°–208°. The material appeared pure by thin layer chromatography on silica gel: 30% ethyl acetate/hexanes, $R_f=0.14$; 5% methanol/dichloromethane, $R_f=0.2$. IR(CHCl$_3$), NMR (CDCl$_3$) and mass spectra (MH+ =502) were consistent with the assigned structure.

ANALYSIS: Calculated for $C_{27}H_{39}N_3O_6$: 64.65% C, 7.84% H, 8.38% N. Found: 64.67% C, 7.85% H, 8.31% N.

EXAMPLE 6

Preparation of 7-Desacetyl-7-(pyrimidin-2-yl)forskolin

A solution of 1.0 g (1.99 mmol) of 7-desacetyl-7-(pyrimidin-2-yl)forskolin 1,9-dimethylformamide acetal (prepared as described in Example 5) was dissolved in a solution of methanol/water (3/1) and stirred at 50°–60° for 72 hr. The solution was allowed to cool to room temperature and was concentrated to a viscous oil. The oil was dissolved in ethyl acetate and flash chromatographed on silica gel, eluting with 30% ethyl acetate/hexanes. The product-containing fractions were combined and concentrated to provide a white solid. The solid was dried under vacuum to provide 0.69 g (1.55 mol, 77.9%) of 7-desacetyl-7-(pyrimidin-2-yl)forskolin mp 194–198. The material appeared pure by thin layer chromatography on silica gel: 1/1 ethyl acetate/hexanes, $R_f=0.29$; 5% methanol/dichloromethane, $R_f=0.18$. IR(CHCl$_3$), NMR (CDCl$_3$) and mass spectra (MH+ =447) were consistent with the assigned structure.

ANALYSIS: Calculated for $C_{24}H_{34}N_2O_6$: 64.55% C, 7.67% H, 6.28% N. Found: 64.30% C, 7.64% H, 6.18% N.

EXAMPLE 7

Preparation of
7-(2-chloropyrimidin-4-yl)-7-desacetylforskolin
1,9-dimethylformamide acetal To a stirred solution of 10 g (23.6 mmol) of 7-desacetylforskolin 1,9-dimethylformamide acetal and 10 g (67.1 mmol) 2,4-dichloropyrimidine in 200 ml of dry tetrahydrofuran in an ice bath was added portion-wise over 10 min 2.65 g (23.7 mmol) of potassium t-butoxide. The mixture was stirred for 0.5 hr, poured into ice/sodium bicarbonate and then extracted with ether. The ether extracts were combined, washed with water, brine, dried over sodium sulfate, filtered and concentrated to an oil. The oil dried by twice azeotroping with toluene on a rotary evaporator. The residual oil was dissolved in 200 ml of dry tetrahydrofuran and the resulting solution was cooled in an ice bath and 2.5 g (22.3 mmol) of potassium t-butoxide followed by 3.5 g (23.5 mmol) of 2,4-dichloropyrimidine were added. The solution was stirred at 0° to 5° for 15 min and worked up as above to provide an oil. The oil was purified by flash chromatography on silica gel, eluting with 10% acetone/hexanes followed by 15% acetone/hexanes to provide 5.66 g (10.6 mmol, 44.9%) of a which was recrystallized from cyclohexane to provide solid 7-(2-chloropyrimidin-4-yl) 7-desacetylforskolin 1,9-dimethylformamide acetal, mp 155°–164°. The material appeared pure by thin layer chromotography on silica gel: 30% acetone/hexanes, $R_f$=0.22; 1/1 ethyl acetate/hexanes, $R_f$=0.50. IR(CHCl$_3$), NMR(CDCl$_3$) and mass spectra (MH+ =536) were consistent with the assigned structure.

ANALYSIS: Calculated for $C_{27}H_{38}ClN_3O_8$: 60.60% C 7.15% H 7.84% N. Found: 60.56% C 7.26% H 7.83% N.

EXAMPLE 8

Preparation of 7-Desacetyl-7-(1-methylpurin-6-yl)forskolin

To a stirred solution of 7-desacetylforskolin 1,9-dimethylformamide acetal (1.5 g, 3.5 mmol) in 30 ml of tetrahydrofuran was added potassium t-butoxide (0.47 g, 4.2 mmol). After stirring for 15 min, 6-chloro-1-methylpurine (0.705 g, 4.2 mmol) was added in one portion. The reaction was quenched with water after 2 hr and extracted with methylene chloride (2×50 ml). The extracts were dried over sodium sulfate and concentrated. The residue was purified by chromatography on silica gel, eluting with hexane/acetone (1:1). The product-containing fractions were combined and concentrated and the resulting residue was crystallized from cyclohexane/ethyl acetate to give (0.9 gram, 46%) of 7-desacetyl-7-(1-methylpurin-6-yl)forskolin 1,9-dimethylformamide acetal. The 1,9-dimethylformamide acetal (550 mg, 0.99 mmol) was heated at 60° in 10/3 methanol/water for 48 hr. The mixture was allowed to cool and extracted with methylene chloride (2×50 ml). The extracts were dried over sodium sulfate and concentrated to give an off-white solid. The solid was purified by flash chromatography, eluting with 5% methanol/methylene chloride and the product-containing fractions were collected, combined, concentrated and the residue was crystallized from hexane/ethyl acetate to provide 250 mg (50.5%) of 7-desacetyl-7-(1-methylpurin-6-yl)forskolin, mp 183°. The material appeared pure by thin layer chromatography on silica gel: 5% methanol/methylene chloride, $R_f$=0.22; hexane/acetone (1:1), $R_f$=0.27. IR(KBr), NMR(DMSO), and mass spectra (MH+ =551) were consistent with the assigned structure.

ANALYSIS: Calculated for $C_{26}H_{36}N_4O_6$: 62.38% C, 7.25% H, 11.19% N. Found: 61.75% C, 7.31% H, 11.11% N.

EXAMPLE 9

Preparation of 7-Desacetyl-7-(4-nitrophenyl)forskolin 1,9-dimethylformamide acetal To a stirred solution of 7-desacetylforskolin 1,9-dimethylformamide acetal (5.0 g, 11.5 mmol) and 1-fluoro-4-nitrobenzene (1.4 g, 13.5 mmol) in 20 ml of tetrahydrofuran was added potassium t-butoxide (1.5 g, 13.5 mmol) in small portions. The addition of base was carried out over a period of 3 hr with the reaction being monitored closely by thin layer chromatography. The reaction was quenched with cold water and extracted with methylene chloride (3×100 ml). The methylene chloride extracts were dried over sodium sulfate and concentrated to give an oil which was purified by flash chromatography on silica gel, eluting with (2:1) hexane/ethyl acetate. The product containing fractions were concentrated to give 1.7 g of 7-desacetyl-7-(4-nitrophenyl) forskolin 1,9-dimethylformamide acetal as an amorphous material. The material appeared pure by thin layer chromatography on silica gel: (2:1) hexane/ethyl acetate, $R_f$=0.42; 1% methanol/methylene chloride, $R_f$=0.17. NMR (CDCl$_3$) IR(CHCl$_3$) and mass spectra (MH+ =545) were consistent with the assigned structure.

ANALYSIS: Calculated for $C_{29}H_{40}N_2O_8$: 63.95% C, 7.40% H, 5.14% N. Found: 64.29% C, 7.35% H, 4.95% N.

EXAMPLE 10

Preparation of 7-Desacetyl-7-(2,4-dinitrophenyl)forskolin 1,9-dimethylformamide acetal To a stirred solution of 7-desacetylforskolin 1,9-dimethylformamide acetal (5.0 g, 11.5 mmol) and 2,4-dinitrofluorobenzene (2.5 g, 13.5 mmol) in 20 ml of tetrahydrofuran was added potassium t-butoxide (1.5 g, 13.5 mmol) in small portions. The addition of base was carried out over a period of 4 hr with the reaction being monitored closely by thin layer chromatography. The reaction was quenched with cold water and extracted with methylene chloride (3×100 ml). The methylene chloride extracts were dried over sodium sulfate and concentrated to an oil which was purified by flash chromatography on silica gel, eluting with (3:1) hexane/ethyl acetate. The product-containing fractions were concentrated to give 2.9 g of 7-desacetyl-7-(2,4-dinitrophenyl) forskolin 1,9-dimethylformamide acetal. The amorphous material appeared pure by thin layer chromatography on silica gel: (2:1) hexane/ethyl acetate, $R_f$=0.38; 1% methanol/methylene chloride, $R_f$=0.25. NMR (CDCl$_3$), IR (CHCl$_3$) and mass spectra (MH+ =590) were consistent with the assigned structure.

ANALYSIS: Calculated for $C_{29}H_{39}N_3O_{10}$: 59.07% C, 6.67% H, 7.13% N. Found: 59.07% C, 6.76% H, 6.96% N.

EXAMPLE 11

Preparation of 7-Desacetyl methylpurin-6-yl) forskolin 1,9 dimethylformamide acetal To a stirred solution of 1.5 g (3.5 mmol) of 7-desacetylforskolin 1,9-dimethylformamide acetal in 30 ml dry tetrahydrofuran was added 0.47 g (4.2 mmol) of potassium t-butoxide. The mixture was allowed to stir for 15 min and then 0.71 g (4.2 mmol) of 6-chloro-1-methylpurine was added and stirring was continued for 2 hr. The reaction mixture was quenched with water and then extracted with methylene chloride. The extracts were combined, dried over sodium sulfate, filtered and concentrated in vacuo. The residue was purified by flash chromatography on silica gel, eluting with 1:1 acetone: hexane. Product-containing fractions were combined and concentrated to give 1.5 g of an amorphous solid. The solid was crystallized from cyclohexane/ethyl acetate to give 0.9 g (77%) of 7-desacetyl-7-(1-methylpurin-6-yl) forskolin 1,9 dimethylformamide acetal, mp 167°. NMR indicated the presence of a compound with the assigned structure as well as a trace of a side product.

ANALYSIS: Calculated for $C_{29}H_{41}N_5O_6$: 62.67% C, 7.45% H, 12.60% N. Found: 60.37% C, 6.91% H, 14.44% N.

EXAMPLE 12

Preparation of 7-Desacetyl-6-(2-dimethylaminoethyl)aminocarbonyl)-7-(pyridin-2-yl)forskolin 1,9-dimethylformamide acetal To a stirred solution of 1.50 g (2.79 mmol) of 7-desacetyl-6-(2-dimethylaminoethylaminocarbonyl)forskolin 1,9-dimethylformamide acetal in 25 ml of tetrahydrofuran was added 0.313 g (2.79 mmol) of potassium t-butoxide. The suspension was stirred at room temperature for 2-3 min after which 0.36 ml (4.19 mmol) of 2-fluoropyridine was added. The mixture was heated to 70° under nitrogen and subsequently stirred for 20 min. To the mixture was added an additional 0.25 ml (2.91 mmol) of 2-fluoropyridine, and the mixture was subsequently stirred for 10 min. The solution was allowed to cool to room temperature, poured into ice/water/sodium bicarbonate/ethyl acetate and the organic layer was separated, washed with saturated sodium chloride, dried over sodium sulfate, filtered and concentrated to an oil. The oil was dissolved in a minimum volume of 1/1 acetone/hexane and flash chromatographed on silica gel, eluting with 1/1 ethyl acetate/hexane, followed by 60% ethyl acetate/hexane. The pure product-containing fractions were combined and concentrated to provide, after drying for 2 hr at 110°, 481 mg (0.782 mmol, 28%) of 7-desacetyl-6-(2-(dimethylamino)ethylaminocarbonyl)-7-(pyridin-2-yl)forskolin 1,9-dimethylformamide acetal, as an oil. The material appeared pure by thin layer chromatography on silica gel: 1/1 acetone/hexane, $R_f$=0.1; 10% methanol/dichloromethane, $R_f$=0.1. IR(CHCl$_3$), NMR(CDCl$_3$) and mass spectra (MH+ =615) were consistent with the assigned structure.

ANALYSIS: Calculated for $C_{33}H_{50}N_4O_7$: 64.47% C, 8.20% H, 9.11% N. Found: 63.99% C, 8.11% H, 7.91% N.

EXAMPLE 13

Preparation of 7-Desacetyl-6-((2-dimethylamino)ethylaminocarbonyl)-7-(pyridin-2-yl)forskolin hydrochloride hydrate 7-Desacetyl-6-((2-dimethylamino)ethylaminocarbonyl)-7-(pyridin-2-yl)forskolin 1,9-dimethylformamide acetal (prepared as described in Example 12) (450 mg, 0.804 mmol) was dissolved in a minimum volume of methanol and the solution diluted with 50 ml of 3/1 methanol/water. The solution was stirred for 18 hr under nitrogen at 60°-65°, and subseqently at 75°-80° for 6 hr. The solution was allowed to cool to room temperature and concentrated to provide a white solid (0.395 g). The solid was recrystallized from 95% ethanol (two crops), washed with hot water and dried under high vacuum at 80°. The dried white solid was dissolved in methanol and treated with ethereal hydrogen chloride until just acidic. The solvent was evaporated under high vacuum and the residue triturated with ether. The resulting white solid was dried at 110° for 2 hr. to provide 143 mg (0.233 mmol, 29% of 7-desacetyl-6-(2-dimethylaminoethylaminocarbonyl)-7-(pyridin-2-yl)forskolin hydrochloride hydrate, mp 175°-195°. The material appeared pure by thin layer chromatography on silica gel: 10% methanaol/dichloromethane, $R_f$=0.1; 2/1 acetone/hexane, $R_f$=0.11. IR(KBr), NMR(DMSO-d$_6$) and mass spectra (MH+ =560) were consistent with the assigned spectra.

ANALYSIS: Calculated for $C_{30}H_{48}ClN_3O_8$: 58.66% C, 7.88% H, 6.84% N. Found: 58.59% C, 7.57% H, 6.65% N.

EXAMPLE 14

Preparation of 7-Desacetyl-6-(3-dimethylaminopropylaminocarbonyl)-7-(pyrimidin-2-yl)forskolin 1,9-dimethylformamide acetal To a stirred solution of 1.0 g (1.8 mmol) of 7-desacetyl-6-[(3-dimethylaminopropyl)aminocarbonyl]forskolin 1,9-dimethylformamide acetal in 10 ml of tetrahydrofuran was added 244 mg (2.1 mmol) of potassium t-butoxide. The suspension was stirred for 20 min before the addition of 250 mg (2.1 mmol) of 2-chloropyrimidine. The mixture was stirred overnight, quenched with water (50 ml) and extracted with methylene chloride (3×50 ml). The extracts were dried over sodium sulfate and concentrated to an oil which was purified by chromatography on silica gel, eluting with 30% methanol/methylene chloride. The product containing and fractions were collected and the solvent was removed to give 370 mg (33%) of 7-desacetyl-6-(3-dimethylaminopropylaminocarbonyl)-7-(pyrimidin-2-yl) forskolin 1,9-dimethylformamide acetal. The material appeared pure by thin layer chromatography on silica gel: 10% methanol/methylene chloride, $R_f$=0.08; 20% methanol/methylene chloride, $R_f$=0.2. IR(CHCl$_3$), NMR(CDCl$_3$), and mass spectra (MH+ =630) were consistent for the assigned structure.

ANALYSIS: Calculated for $C_{33}H_{51}N_5O_7$: 62.94% C, 8.16% H, 11.12% N. Found: 62.42% C, 8.20% H, 10.80% N.

EXAMPLE 15

Preparation of 7-Desacetyl-6-((2-dimethylamino)ethylaminocarbonyl)-7-(pyrimidin-2-yl)forskolin hydrochloride hydrate A stirred solution of 2.0 g (3.2 mmol) of 7-desacetyl-6-(2-dimethylaminoethylaminocarbonyl)-7-(pyrimidin-2-yl)forskolin 1,9-dimethylformamide acetal in 30 ml of methanol and 10 ml of water was heated at 60° for 48 hr. The mixture was allowed to cool to room temperature after which 100 ml of methylene chloride and 50 ml of water were added. The organic layer was separated, dried over sodium sulfate and the methylene chloride was removed in vacuo. The crude product was crystallized from methanol/ether to give 1.35 g (74%) of 7-desacetyl-6-(2-dimethylaminoethylaminocarbonyl)-7-(pyrimidin-2-yl)forskolin. A portion (350 mg) was dissolved in hot ethanol and ethereal hydrogen chloride was added until the solution became acidic. Concentration and recrystallization gave the hydrochloride salt, mp 180° (dec.) The free base of the material appeared pure by thin layer chromatography on silica gel: 30% methanol/methylene chloride, $R_f$=0.44; 10% methanol/methylene chloride, $R_f$=0.14. NMR(DMSO), IR(KBr) and mass spectra (MH+ =561) were consistent with the assigned structure.

ANALYSIS: Calculated for $C_{29}H_{44}N_4O_7$ HCl H$_2$O: 56.61% C, 7.71% H, 9.10% N. Found: 56.74% C, 7.63% H, 9.00% N.

EXAMPLE 16

Preparation of 7-desacetyl-6-(2-dimethylaminoethyl)aminocarbonyl-7-(pyrimidin-2-yl)forskolin 1,9-dimethylformamide acetal To a stirred solution of 7-desacetyl-6-(2-dimethylaminoehtyl)aminocarbonylforskolin 1,9-dimethylformamide acetal (3.0 g, 5.6 mmol) in dry tetrahydrofuran (30 ml) was added potassium t-butoxide (750 mg, 6.7 mmol) in one portion followed, after 15 min, by 2-chloropyrimidine (760 mg, 6.7 mmol). After stirring for 2 hr, additional potassium t-butoxide (300 mg) was added and the reaction was allowed to stir overnight. Ice and water were added to the reaction mixture followed by methylene chloride (100 ml), the layers were separated and the aqueous portion was extracted with additional methylene chloride. The organic layers were combined, dried over sodium sulfate, concentrated and then purified by flash chromatography on silca gel, eluting with 10% methanol/methylene chloride. The product containing fractions were collected and the solvent removed to give 7-desacetyl-6-(2-dimethylaminoethyl)aminocarbonyl-7-(pyrimidin-2-yl)forskolin 1,9-dimethylformamide acetal (1.2 g, 35%). The material appeared pure by thin layer chromatography on silica gel: 10% methanol/methylene chloride, $R_f=0.16$; 30% methanol/methylene chloride, $R_f=0.47$. IR(CHCl$_3$), NMR (CDCl$_3$) and mass spectra (MH$^+$ =615) are consistent with the assigned structure.

ANALYSIS: Calculated for $C_{32}H_{49}N_5O_7$: 62.40% C, 8.03% H, 11.37%. Found: 62.09% C, 8.02% H, 11.27%.

EXAMPLE 17

Preparation of 7-desacetyl-6-(3-dimethylaminopropyl)aminocarbonyl-7-(pyrimidin-2-yl)forskolin 7-Desacetyl-6-(3-dimethylaminopropyl)aminocarbonyl-7-(pyrimidin-2-yl)forskolin 1,9-dimethylformamide acetal (1.0 g, 1.58 mmol) was dissolved in methanol (100 ml and water (30 ml). The resulting solution was heated at 60° C. under nitrogen atmosphere for 3 days. The reaction mixture was allowed to cool to room temperature and extracted with methylene chloride (100 ml, 50 ml). The extracts were dried over sodium sulfate and the solvent removed to give a white solid which was crystallized from methanol to give 7-desacetyl-6-(3-dimethylaminopropyl)aminocarbonyl-7-(pyrimidin-2-yl)forskolin (450 mg, 49%). The material appeared pure by thin layer chromatography on silica gel: $R_f=0.04$, 10% methanol/methylene chloride; $R_f=0.12$, 30% methanol/methylene chloride. NMR(CDCl$_3$, DMSO) and mass spectrum (MH$^+$ =575) are consistent with the assigned structure.

ANALYSIS: Calculated For $C_{30}H_{46}N_4O_7$: 62.68% C, 8.08% H, 9.74% N. Found: 62.06% C, 8.01% H, 9.07% N.

REACTION SCHEME A

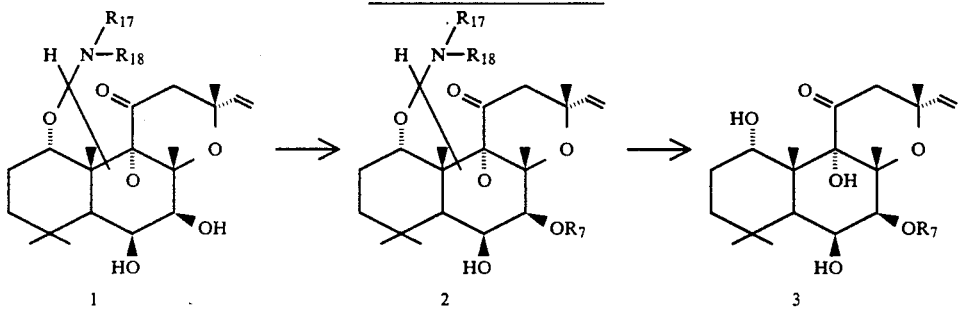

REACTION SCHEME B

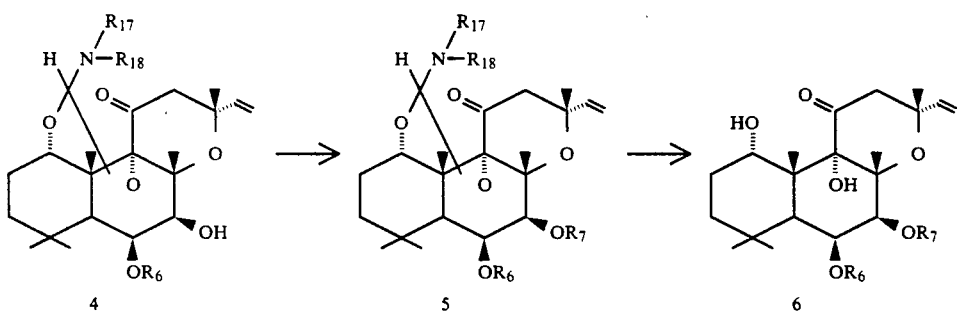

We claim:

1. A compound of formula

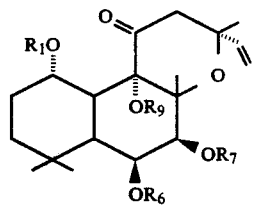

wherein

R$_1$ and R$_9$ taken together form a group of formula CHNR$_{17}$R$_{18}$;

R$_6$ is hydrogen, a group of formula R$_{13}$CO or a group of formula CONR$_{14}$R$_{15}$;

R$_7$ is phenyl, naphthyl, furanyl, oxazolyl, thiazolyl, pyridinyl, pyrimidinyl, purinyl, quinolinyl or isoquinolinyl, each of which is unsubstituted or mono- or poly-substituted by loweralkyl, halogen or nitro;

$R_{13}$ is hydrogen or loweralkyl;

$R_{14}$ is hydrogen, loweralkyl, hydroxyloweralkyl, loweralkoxyloweralkyl, or a group of formula $HOCH_2CH(OH)CH_2$;

$R_{15}$ is hydrogen, loweralkyl, hydroxyloweralkyl, loweralkoxyloweralkyl, a group of formula

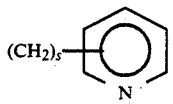

wherein s is 1 or 2, a group of formula

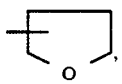

a group of formula $HOCH_2CH(OH)CH_2$, or a group of formula $(CH_2)_tNR_{21}R_{22}$ wherein t is an integer from 2 to 6;

$R_{17}$ and $R_{18}$ are the same or different and each is loweralkyl;

$R_{21}$ and $R_{22}$ are the same or different and each is loweralkyl; or $R_{21}$ and $R_{22}$ taken together with the nitrogen atom to which they are attached form a group of formula

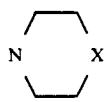

wherein X is CO, O, S, $CHR_{23}$ or $NR_{24}$;

$R_{23}$ is hydrogen, loweralkyl or $OR_{25}$;

$R_{24}$ is loweralkyl;

$R_{25}$ is hydrogen or $COR_{26}$;

$R_{26}$ is loweralkyl; and the optical and geometric isomers thereof, or a pharmaceutically acceptable salt thereof.

2. A compound according to claim 1 wherein:

$R_6$ is hydrogen or a group of formula $CONR_{14}(CH_2)_tNR_{21}R_{22}$;

$R_7$ is phenyl, pyridinyl, pyrimidinyl or purinyl, each of which is unsubstituted or mono- or poly-substituted by loweralkyl, halogen or nitro;

$R_{14}$ is hydrogen or loweralkyl; and $R_{17}$, $R_{18}$, $R_{21}$ and $R_{22}$ are the same or not all the same and each is hydrogen or loweralkyl.

3. A compound according to claim 1 wherein $R_1$ and $R_9$ taken together form a group of formula $CHN(CH_3)_2$.

4. A compound according to claim 3 wherein $R_6$ is hydrogen.

5. A compound according to claim 3 wherein $R_6$ is $CONR_{14}(CH_2)_tNR_{21}R_{22}$.

6. A compound according to claim 5 wherein $R_6$ is $CONH(CH_2)_tN(CH_3)_2$ and t is 2 or 3.

7. The compound of claim 4 which is 7-desacetyl-7-(pyridin-2-yl)forskolin 1,9-dimethylformamide acetal.

8. The compound of claim 4 which is 7-desacetyl-7-(pyrimidin-2-yl)forskolin 1,9-dimethylformamide acetal.

9. The compound of claim 4 which is 7-desacetyl-7-(6-fluoropyridin-2-yl)forskolin 1,9-dimethylformamide acetal.

10. The compound of claim 4 which is 7-desacetyl-7-(4-nitrophenyl)forskolin 1,9-dimethylformamide acetal.

11. The compound of claim 4 which is 7-desacetyl-7-(2,4-dinitrophenyl)forskolin 1,9-dimethylformamide acetal.

12. The compound of claim 4 which is 7-desacetyl-7-(1-methylpurin-6-yl)forskolin 1,9-dimethylformamide acetal.

13. The compound according to claim 4 which is 7-desacetyl-6-(3-dimethylaminopropylaminocarbonyl)-7-(pyrimidin-2-yl)forskolin 1,9-dimethylformamide acetal.

14. The compound according to claim 5 which is 7-desacetyl-6-(2-dimethylaminoethylaminocarbonyl)-7-pyridin-2-yl)forskolin 1,9-dimethylformamide acetal.

15. The compound according to claim 5 which is 7-(2-chloropyrimidin-4-yl)-7-desacetylforskolin 1,9-dimethylformamide acetal.

16. The compound according to claim 5 which is 7-desacetyl-6-(2-dimethylaminoethyl)aminocarbonyl-7-(pyrimidin-2-yl)forskolin 1,9-dimethylformamide acetal.

* * * * *